United States Patent
Robinson et al.

(10) Patent No.: US 10,335,124 B1
(45) Date of Patent: Jul. 2, 2019

(54) MARKER DELIVERY DEVICE WITH ADAPTOR FOR BIOPSY SITE MARKING AND METHOD OF USE THEREOF

(71) Applicant: DEVICOR MEDICAL PRODUCTS, INC., Cincinnati, OH (US)

(72) Inventors: Andrew Robinson, Cincinnati, OH (US); Emmanuel Tanghal, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 149 days.

(21) Appl. No.: 15/445,553

(22) Filed: Feb. 28, 2017

Related U.S. Application Data

(60) Provisional application No. 62/301,503, filed on Feb. 29, 2016.

(51) Int. Cl.
*A61B 5/05* (2006.01)
*A61B 10/02* (2006.01)
(Continued)

(52) U.S. Cl.
CPC .......... *A61B 10/02* (2013.01); *A61B 17/3468* (2013.01); *A61B 90/39* (2016.02);
(Continued)

(58) Field of Classification Search
CPC ..... A61B 10/02; A61B 17/3468; A61B 90/39; A61B 2017/00477; A61B 2090/3925;
(Continued)

(56) References Cited

U.S. PATENT DOCUMENTS 5,526,822 A   6/1996   Burbank et al.
6,086,544 A   6/2000   Hibner et al.
(Continued)

FOREIGN PATENT DOCUMENTS

DE   10 2004 012226 A1   9/2005

OTHER PUBLICATIONS

Mammotome®, Biopsy Site Identifiers—for predictable placement and rapid expansion, downloaded from http://www.mammotome.com/, Nov. 20, 2015, 3 pgs.
(Continued)

*Primary Examiner* — Rex R Holmes
(74) *Attorney, Agent, or Firm* — Frost Brown Todd LLC

(57) ABSTRACT

A marker delivery device includes a cannula with a first end, a second end, a marker exit near the second end, a handle into which the cannula extends or to which the cannula is attached, the cannula being capable of receiving a plunger and rod that are operable to deploy a marker from the marker exit, the marker delivery device further including a tapered adaptor portion attached to or surrounding the cannula and abutting the handle. The tapered adaptor portion is configured to engage a plurality of different sleeves for differing biopsy devices. Various aspects offer improved ease of removal from commercially available biopsy devices due to its "pinch release" feature. Various aspects of the device allow use with multiple commercially available biopsy devices so as to ensure proper positioning of the devices for marker deployment.

25 Claims, 11 Drawing Sheets

(51) Int. Cl.
*A61B 90/00* (2016.01)
*A61B 17/34* (2006.01)
*A61B 17/00* (2006.01)

(52) U.S. Cl.
CPC ............... *A61B 2017/00477* (2013.01); *A61B 2090/3925* (2016.02); *A61B 2090/3937* (2016.02); *A61B 2090/3954* (2016.02); *A61B 2090/3966* (2016.02); *A61B 2090/3987* (2016.02)

(58) Field of Classification Search
CPC .... A61B 2090/3937; A61B 2090/3954; A61B 2090/3987; A61B 2090/3966
See application file for complete search history.

(56) References Cited

U.S. PATENT DOCUMENTS

| | | | |
|---|---|---|---|
| 6,083,524 A | 7/2000 | Sawhney et al. | |
| 6,162,241 A | 12/2000 | Coury et al. | |
| 6,177,095 B1 | 1/2001 | Sawhney et al. | |
| 6,228,055 B1 | 5/2001 | Foerster et al. | |
| 6,270,464 B1 | 8/2001 | Fulton, III et al. | |
| 6,356,782 B1 | 3/2002 | Sirimanne et al. | |
| 6,371,904 B1 | 4/2002 | Sirimanne et al. | |
| 6,605,294 B2 | 8/2003 | Sawhney | |
| 6,626,849 B2 | 9/2003 | Huitema et al. | |
| 6,790,185 B1 | 9/2004 | Fisher et al. | |
| 6,993,375 B2 | 1/2006 | Burbank et al. | |
| 6,996,433 B2 | 2/2006 | Burbank et al. | |
| 7,044,957 B2 | 5/2006 | Foerster et al. | |
| 7,047,063 B2 | 5/2006 | Burbank et al. | |
| 7,229,417 B2 | 6/2007 | Foerster et al. | |
| RE39,713 E | 7/2007 | Sawhney et al. | |
| 7,442,171 B2 | 10/2008 | Stephens et al. | |
| 7,465,279 B2 | 12/2008 | Beckman et al. | |
| 7,507,210 B2 | 3/2009 | Hibner et al. | |
| 7,668,582 B2 | 2/2010 | Sirimanne et al. | |
| 7,938,786 B2 | 5/2011 | Ritchie et al. | |
| 8,068,895 B2 | 11/2011 | Speeg et al. | |
| 8,118,755 B2 | 2/2012 | Hibner et al. | |
| 8,241,299 B2 | 8/2012 | Hibner | |
| 8,251,916 B2 | 8/2012 | Speeg et al. | |
| 8,306,602 B2 | 11/2012 | Sirimanne et al. | |
| 8,320,993 B2 | 11/2012 | Sirimanne et al. | |
| 8,371,443 B2 | 2/2013 | Nock et al. | |
| 8,414,602 B2 | 4/2013 | Selis | |
| 8,532,747 B2 | 9/2013 | Nock et al. | |
| 8,600,481 B2 | 12/2013 | Sirimanne et al. | |
| 9,095,326 B2 | 8/2015 | Ritchie et al. | |
| 2005/0283069 A1 | 12/2005 | Hughes et al. | |
| 2008/0033280 A1* | 2/2008 | Lubock | A61B 17/3468 600/414 |
| 2011/0071391 A1 | 3/2011 | Speeg | |
| 2013/0172920 A1 | 7/2013 | Euteneuer et al. | |
| 2013/0237912 A1 | 9/2013 | Speeg | |
| 2014/0276037 A1 | 9/2014 | Johnson et al. | |

OTHER PUBLICATIONS

Extended European Search Report of related European Patent Application No. 16159618.4 dated Oct. 18, 2016.
Bard Marker Devices, as viewed on Feb. 28, 2017. http://www.bardbiopsy.com/products/index_markers.php.
Marker Devices, as viewed on Feb. 28, 2017, http://www.hologic.com/products/intervention-and-treatment/breast-biopsy/breastbiopsy-markers-stereotactic.

* cited by examiner

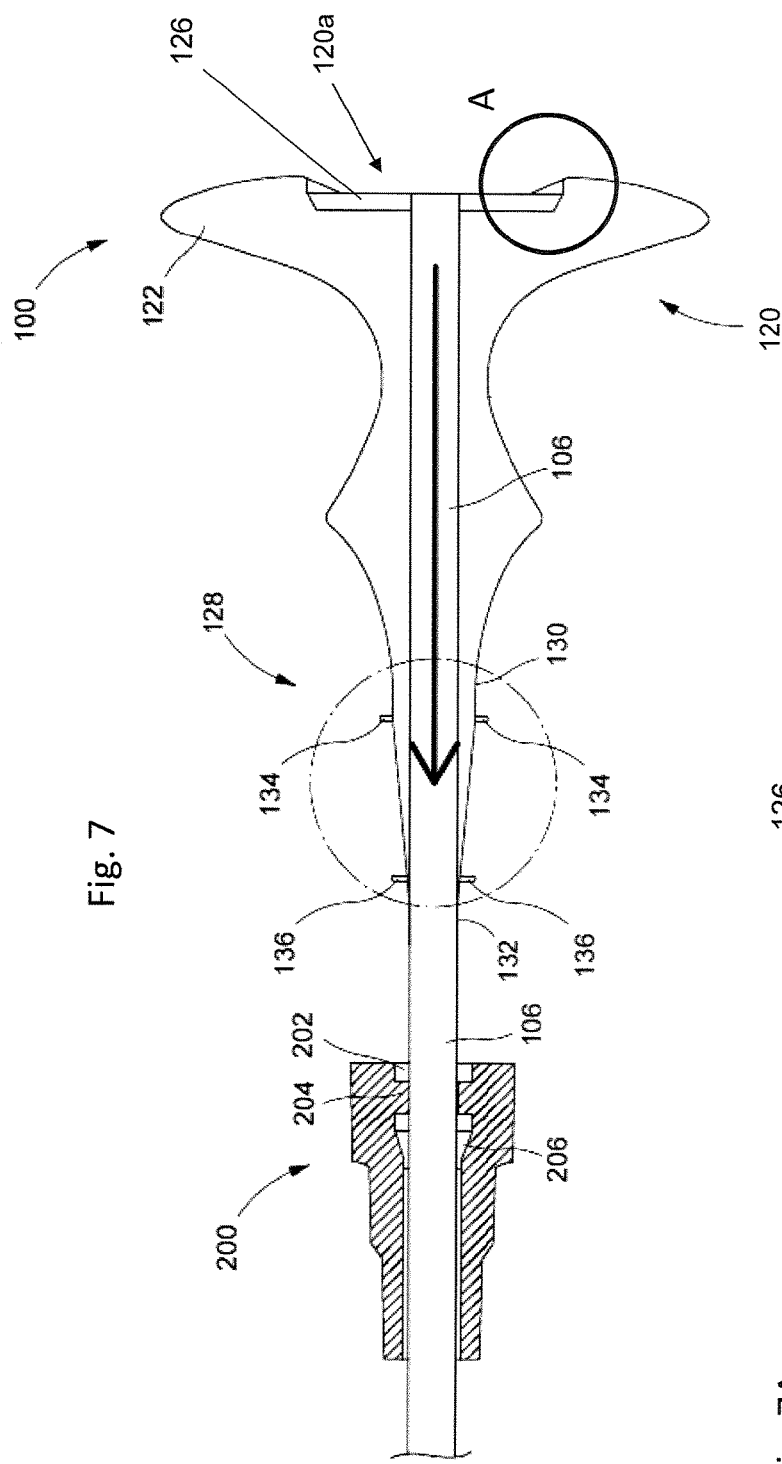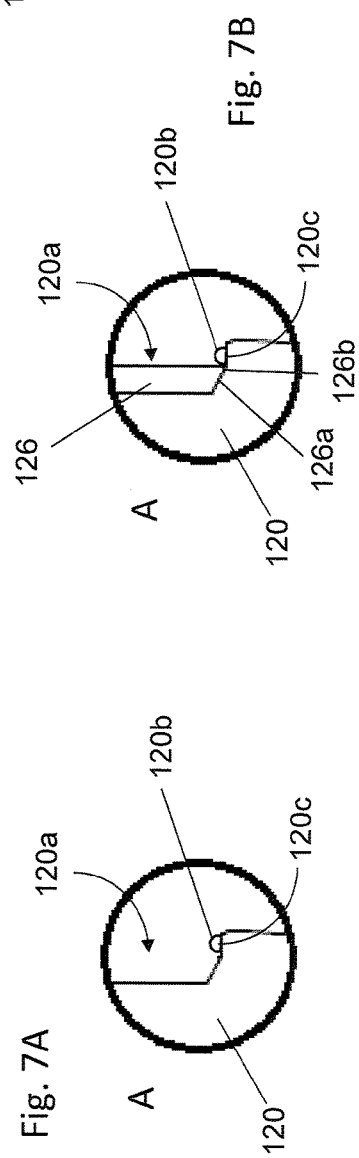
Fig. 7
Fig. 7A
Fig. 7B

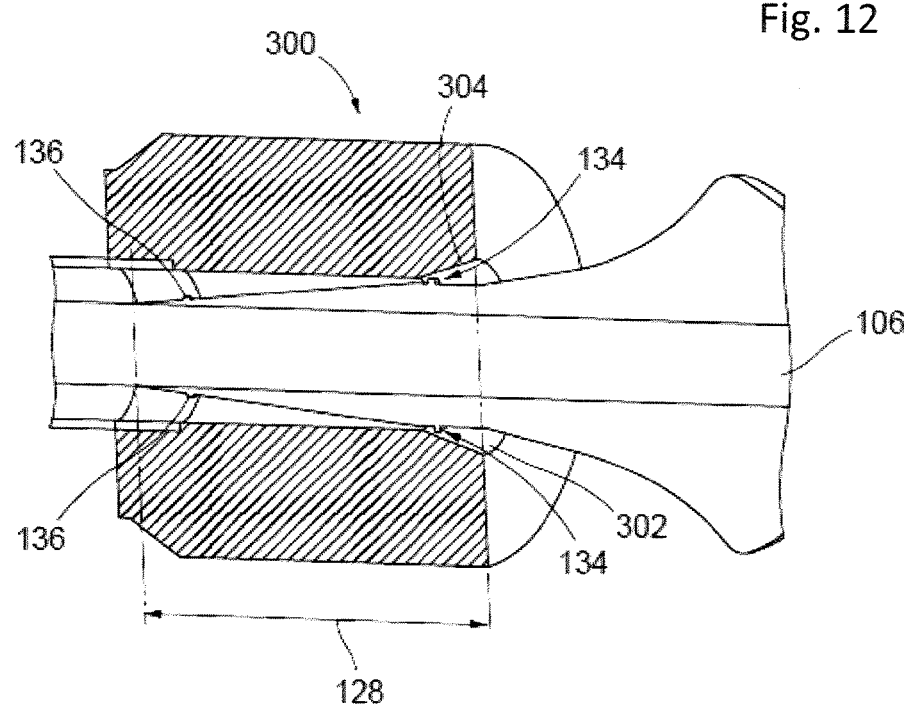
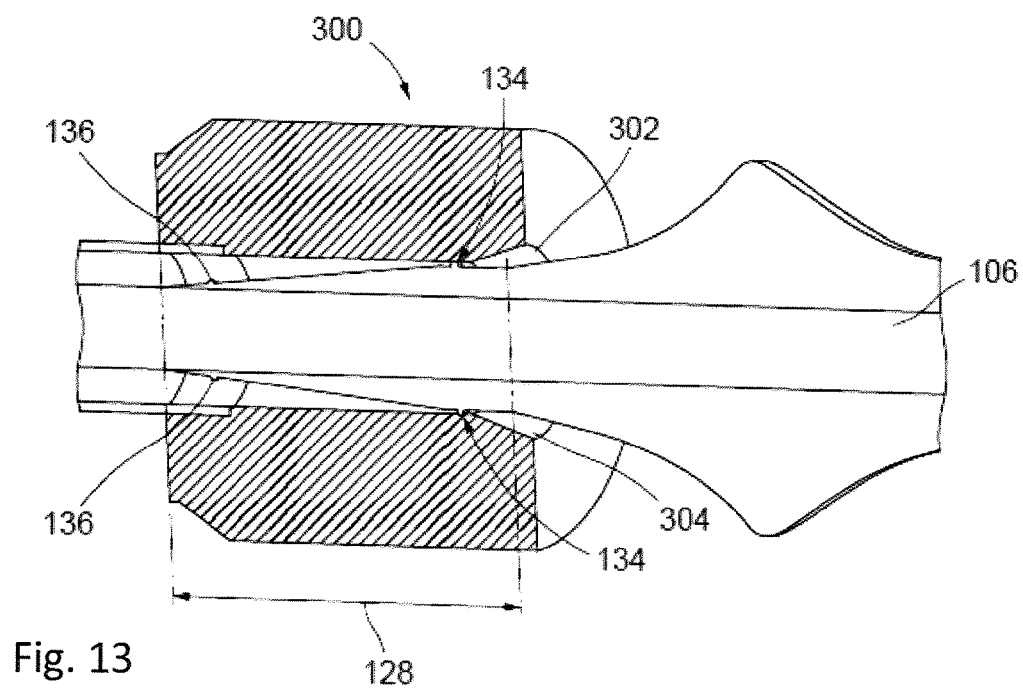
Fig. 12
Fig. 13

MARKER DELIVERY DEVICE WITH ADAPTOR FOR BIOPSY SITE MARKING AND METHOD OF USE THEREOF

This application claims priority to U.S. Provisional Patent Application No. 62/301,503, titled "Marker Delivery Device with Adaptor for Breast Biopsy Site Marking," filed on Feb. 29, 2016, the entirety of which is hereby incorporated herein by reference.

BACKGROUND

Field

Aspects of the present disclosure relate generally to marker delivery devices for breast biopsy site marking, and in particular to marker applicators for marking breast biopsy sites.

Background

Biopsy samples have been obtained in a variety of ways in various medical procedures using a variety of devices. Biopsy devices may be used under stereotactic guidance, ultrasound guidance, Magnetic Resonance Imaging (MRI) guidance, Positron Emission Mammography (PEM) guidance, Breast-Specific Gamma Imaging ("BSGI") guidance, or otherwise.

Example biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,626,849, entitled "MRI Compatible Surgical Biopsy Device," issued Sep. 30, 2003; U.S. Pat. No. 7,442,171, entitled "Remote Thumbwheel for a Surgical Biopsy Device," issued Oct. 28, 2008; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 21, 2012; U.S. Pat. No. 8,251,916, entitled "Revolving Tissue Sample Holder for Biopsy Device," issued Aug. 28, 2012; U.S. Pat. No. 8,532,747, entitled "Biopsy Marker Delivery Device," issued Sep. 10, 2013; and U.S. Pat. No. 9,095,326, entitled "Biopsy System with Vacuum Control Module," issued Aug. 4, 2015. The disclosure of each of the above-cited U.S. Patents and U.S. Patent Application Publications is incorporated by reference herein.

It is typical in the related art to mark the location of a biopsy site for future reference. For instance, one or more markers may be deposited at a biopsy site before, during, or after a tissue sample is taken from the biopsy site. Example markers are commercially available and include, but are not limited to, the MAMMOMARK™, MICROMARK®, CORMARK™, HYDROMARK, and MAMMOSTAR brand marker devices available from Devicor Medical Products, Inc. of Cincinnati, Ohio, see http://www.mammotome.com/. Other commercially available marker devices are available from Hologic Inc. as SecureMark® and TriMark® biopsy site markers. See http://www.hologic.com/products/intervention-and-treatment/breast-biopsy/breast biopsy-markers-stereotactic. Other commercially available marker devices are available from C.R. Bard Inc. as Gel Mark Ultra™, Gel Mark Ultra Cor™; SenoMark™; SenoMark Ultra™, SenoMark UltraCor™; SenoMark UltraCor MRI; StarchMark®; StarchMark®; UltraCor; UltraClip™; Ultra-Clip Dual Trigger™; and Ultra Cor™ biopsy site markers. See http://www.bardbiopsy.com/products/index_markers.php.

Further example devices and methods for marking a biopsy site are disclosed in U.S. Pat. No. 6,228,055, entitled "Devices for Marking and Defining Particular Locations in Body Tissue," issued May 8, 2001; U.S. Pat. No. 6,356,782 entitled, "Subcutaneous Cavity Marking Device and Method," issued Mar. 12, 2002; U.S. Pat. No. 6,371,904, entitled "Subcutaneous Cavity Marking Device and Method," issued Apr. 16, 2002, U.S. Pat. No. 6,993,375, entitled "Tissue Site Markers for In Vivo Imaging," issued Jan. 31, 2006; U.S. Pat. No. 6,996,433, entitled "Imageable Biopsy Site Marker," issued Feb. 7, 2006; U.S. Pat. No. 7,044,957, entitled "Devices for Defining and Marking Tissue," issued May 16, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; U.S. Pat. No. 7,465,279, entitled "Marker Device and Method of Deploying a Cavity Marker Using a Surgical Biopsy Device," issued Dec. 16, 2008; U.S. Pat. No. 7,668,582, entitled "Biopsy Site Marker," issued Feb. 23, 2010; U.S. Pat. No. 8,306,602, entitled "Biopsy Cavity Marking Device," issued Nov. 6, 2012; U.S. Pat. No. 8,320,993, entitled "Subcutaneous Cavity Marking Device," issued Nov. 27, 2012; U.S. Pat. No. 8,600,481, entitled "Subcutaneous Cavity Marking Device," issued Dec. 3, 2013; U.S. Pat. No. 8,371,443, entitled "Biopsy Marker Delivery Device," issued Sep. 10, 2013; U.S. Pat. No. 8,241,299, entitled "Biopsy Marker Delivery Configured to Retain Marker Prior to Intended Deployment," issued Aug. 14, 2012; U.S. Pat. No. 8,068,895, entitled "Biopsy Site Marker Deployment Instrument," issued Nov. 14, 2011; U.S. Pat. No. 8,414,602, entitled "Biopsy Device and Methods," issued Apr. 9, 2013; and U.S. Pat. Publication No. 2013/0237912, entitled "Biopsy Marker Delivery Device," published Sep. 12, 2013, now abandoned; and U.S. Pat. Publ. No. 2014/0276037, entitled "Biopsy Site Marker Applier," published Sep. 18, 2004. The disclosure of each of the above-cited U.S. Patents and U.S. Patent Application Publications is incorporated by reference herein.

Additional devices and methods of inserting Markers to mark biopsy sites include U.S. Pat. No. 6,083,524, entitled "Polymerizable Biodegradable Polymers including Carbonate or Dioxanone Linkages," issued Jul. 4, 2000; U.S. Pat. No. 6,162,241, entitled "Hemostatic Tissue Sealants," issued Dec. 19, 2000; U.S. Pat. No. 6,177,095, entitled "Polymerizable Biodegradable Polymers Including Carbonate or Dioxanone Linkages," issued Jan. 23, 2001; U.S. Pat. No. 6,270,464 entitled, "Biopsy Localization Method and Device," issued Aug. 7, 2001; U.S. Pat. No. 6,356,782, entitled "Subcutaneous Cavity Marking Device and Method," issued Mar. 12, 2002; U.S. Pat. No. 6,605,294, entitled "Methods of Using In Situ Hydration of Hydrogel Articles for Sealing or Augmentation of Tissue or Vessels," issued Aug. 12, 2003; U.S. Pat. No. 6,790,185, entitled "Sealant Plug Delivery Methods," issued Sep. 14, 2001; U.S. Reissue Pat. No. RE39,713, entitled "Polymerizable Biodegradable Polymers Including Carbonate or Dioxanone Linkages," issued Jul. 3, 2007; U.S. Pat. No. 8,320,993, entitled "Subcutaneous Cavity Marking Device," issued Nov. 27, 2012, and U.S. Pat. No. 8,600,481, entitled "Subcutaneous Cavity Marking Device," issued Dec. 3, 2013. The disclosure of each of the above-cited U.S. Patents and U.S. Patent Application Publications is incorporated by reference herein.

When a suspicious tissue mass is discovered in a patient's body through examination, ultrasound, MRI, X-ray imaging or the like, it is often necessary to perform a biopsy procedure to remove one or more samples of that tissue in order to determine whether the mass contains cancerous cells. A biopsy may be performed using an open or percutaneous method.

A Percutaneous biopsy, is generally much less invasive than open biopsy. Percutaneous biopsies may be performed using fine needle aspiration (FNA) or a core needle biopsy. In an FNA biopsy, a very thin needle is used to withdraw fluid and cells from the suspicious tissue mass. A possible shortcoming of FNA is that only a small number of cells are obtained through the procedure, rendering it relatively less useful in analyzing the suspicious tissue and making an assessment of the progression of the cancer less simple if the sample is found to be malignant.

During a core needle biopsy, a small tissue sample is removed, allowing for a pathological assessment of the tissue, including an assessment of the progression of any cancerous cells that are found. In U.S. Pat. Publication No. 2005/0283069A1, entitled "MRI biopsy device localization fixture" to Hughes et al., filed Apr. 12, 20015, the disclosure of which is hereby incorporated by reference in its entirety, a localization mechanism, or fixture, is described that is used in conjunction with a breast coil for breast compression and for guiding a core biopsy instrument during prone biopsy procedures in both open and closed MRI machines. The localization fixture mentioned above includes a three-dimensional Cartesian positionable guide for supporting and orienting an MRI-compatible biopsy instrument, and, in particular, a sleeve (hereinafter interchangeably referred to as an obturator and/or obturator sleeve) to a biopsy site of suspicious tissues or lesions. After a biopsy is performed, a marker may be deployed into the area of tissue removed during the biopsy procedure. See, e.g., U.S. Pat. No. 7,507,210, entitled "Biopsy Cannula Adjustable Depth Stop" to Hibner, et al., issued Mar. 24, 2009, the disclosure of which is hereby incorporated by reference in its entirety.

When preforming a breast biopsy, for example, patient's breasts may hang pendulously into a breast aperture formed as a lateral recesses of the localization fixture. To enhance hands off use of a biopsy system, for example when repeated reimaging is required within the narrow confines of a closed bore MRI machine, the biopsy system may include a sleeve 94 (e.g., an obturator sleeve), which may be held fixed in relation to the breast aperture and accordingly can be held in a fixed position with relation to the breast to which a procedure is being performed. As shown in FIG. 1 (which reproduces an example fixture shown in FIG. 9 of U.S. Pat. No. 7,507,210 and includes the reference numbers from that patent, which reference numbers are solely applicable to this figure and are not used as reference numbers further in this document), the localization fixture may include a mounted cube grid 104, which may include a plurality of square cross-sectionally shaped recesses 130 that may be dimensioned to receive a plurality of guide cubes 104. Each guide cube may include a single and/or plurality of guide holes or openings for receiving an obturator 94 through a proximal end 142. The guide cube 104 may further include a front face 112 having a stop portion 95 for limiting the movement of the obturator 94 within the guide cube 104.

When performing a procedure of marking a biopsy site using the abovementioned example localization fixture having a grid 96, the process may include first puncturing the tissue with a puncture needle and/or an obturator sleeve 94 having a puncture needle, for example. Next, if a separate puncture needle is used, the puncture needle may be removed from the obturator sleeve 94, with the sleeve 94 being retained in the same position within the grid 96 and the body of a patient (e.g., the tip end of the sleeve 94 may be retained, for example, within a breast undergoing the biopsy procedure). Then, a biopsy device, which may include, for example, a cannular inner cutter, may be inserted into the sleeve 94 to remove a tissue sample from the biopsy site. The biopsy device may then be removed from the sleeve 94, which may remain within the grid 96 and positioned within the target breast tissue. A marker delivery device, for example, may then be inserted into the sleeve 94, via which a marker may be deployed into or near the biopsy site.

However, such sleeves and marker delivery devices often have features that prevent differing types of sleeves from being interchangeably used with differing marker delivery devices, and each type of marker delivery device from being interchangeably used with differing sleeves.

There remains an unmet need for a marker delivery device having one or more features that are capable of being received and properly used within a plurality of differently shaped sleeves. There is a further unmet need for such a marker delivery devices that is capable of being properly received in a plurality of differently shaped sleeves such that the marker outlet of each of the differing marker delivery devices may be readily and easily positioned at or near the same selected location.

SUMMARY

Aspects of the present disclosure provide, among other variations, a marker delivery device (also interchangeably referred to herein as a "marker applicator") comprising: a cannula having a first (also referred to interchangeably herein as a proximal) end, a second (also referred to interchangeably herein as a distal) end, and a marker exit proximate to the second end, wherein the cannula is configured to receive a marker deploying rod for deploying a marker through the marker exit; a handle; and a tapered adaptor portion disposed between the handle and the proximal end of the cannula, the tapered adaptor portion being configured to engage different inner surfaces of a plurality of obturator sleeves into which the tapered adaptor portion is received.

Another aspect of the present disclosure provides a marker delivery device adaptor, comprising: a tapered adaptor portion configured to mate with a sleeve of a biopsy system, wherein the tapered adaptor portion is coaxial with and extends about or from the outer surface of a cannula, the cannula including: a proximal end, a distal end, and a marker exit positioned proximal to the distal end, wherein a rod is receivable within the cannula, the rod being capable of translating within the cannula deploying a marker from the marker exit; wherein the outer surface of the tapered adaptor portion tapers from a first end having a substantially oval cross section to a second end having a substantially circular cross section; and wherein the second end of the tapered adaptor portion is more proximal to the distal end of the cannula than the first end of the cannula.

Another aspect of the present disclosure provides a method of deploying a marker to a biopsy site, comprising: inserting a marker delivery device into an obturator sleeve, the marker delivery device including: a cannula having a first end, a second end, and a marker exit positioned proximal to the second end; a rod being receivable within the cannula; and a tapered adaptor portion coupled to or about the first end of the cannula; engaging the tapered adaptor portion of the marker delivery device with the obturator sleeve via a friction fit; receiving the rod in the cannula; and traversing the received rod so to deploy the marker from the marker exit.

Additional advantages and novel features of various aspects of the present disclosure will be set forth in part in the description that follows, and in part will become more apparent to those skilled in the art upon examination of the following or upon learning by practice thereof.

BRIEF DESCRIPTION OF THE FIGURES

The accompanying drawings, which are incorporated into and constitute a part of this specification, illustrate one or more example aspects of the present disclosure and, together with the detailed description, serve to explain their principles and implementations.

FIG. 7 is a partial cross sectional view of the example marker delivery device of FIG. 2 partially inserted into a first sleeve, with omissions, in accordance with aspects of the present disclosure;

FIG. 7A shows a close up cross-sectional view of a portion of a recess in the handler portion of an example marker delivery device, in accordance with aspects of the present disclosure;

FIG. 7B shows a close up cross-sectional view of the portion of a recess in the handler portion of the example marker delivery device of FIG. 7A with an example plunger button retainably received therein, in accordance with aspects of the present disclosure;

FIG. 12 is a partial close up cross-sectional view of the example marker delivery device of FIG. 2 partially inserted into the second sleeve, in accordance with aspects of the present disclosure;

FIG. 13 is a partial close up cross sectional view of the example marker delivery device of FIG. 2 fully inserted into the second sleeve, in accordance with aspects of the present disclosure;

DETAILED DESCRIPTION

Figure 1:
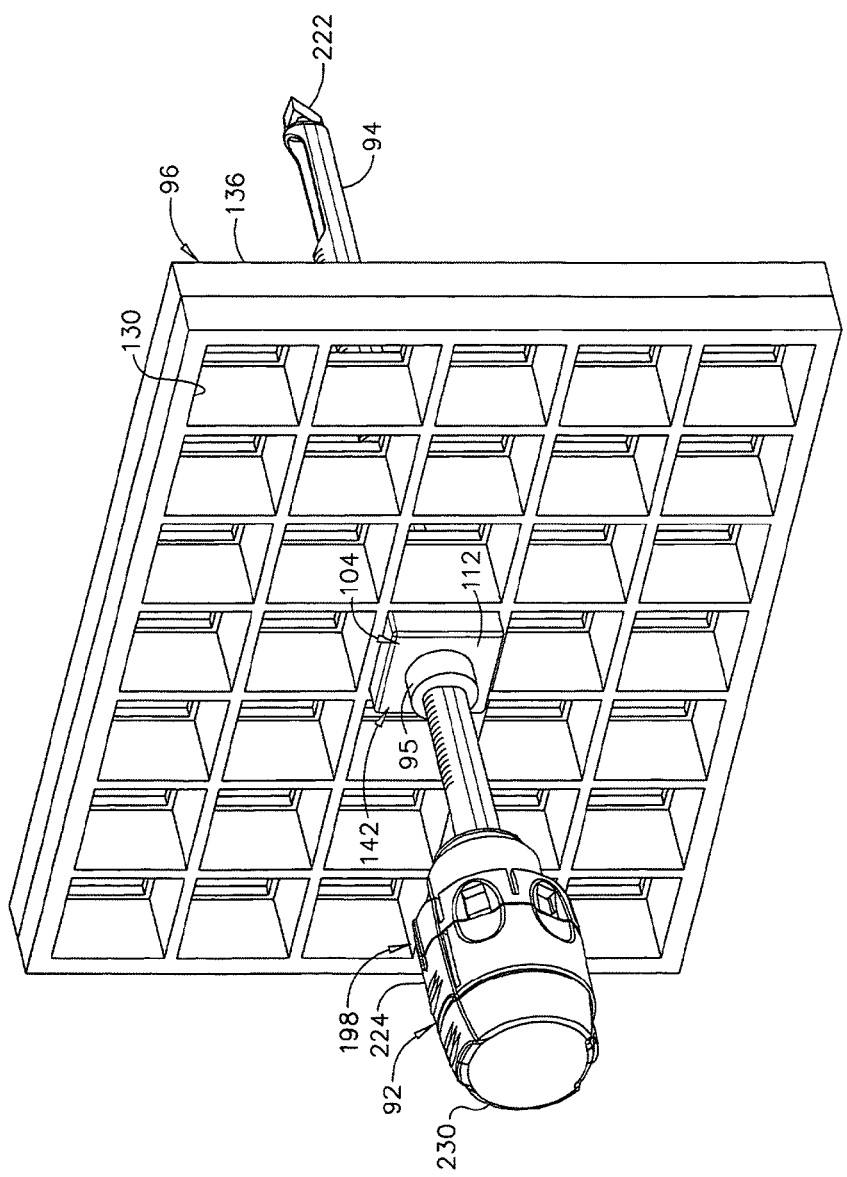
FIG. 1 shows an example localization fixture may include a mounted cube grid for positioning a biopsy device, which may be used in accordance with various aspects of the present disclosure.

The following description of certain examples of the present disclosure should not be used to limit the scope of the present disclosure. Other examples, features, aspects, embodiments, advantages, and one of the best modes contemplated for carrying out various aspects of the present disclosure will become apparent to those skilled in the art from the following description, which is by way of illustration only, and in no way designed to limit the scope of the present disclosure. As will be realized, the present disclosure is capable of other different and obvious aspects, all without departing from the scope hereof. Accordingly, the drawings and descriptions should be regarded as illustrative in nature and not restrictive.

Aspects of the present disclosure provide, among other variations, a marker delivery device (also interchangeably referred to herein as a "marker applicator") comprising: a cannula having a first (also referred to interchangeably herein as a proximal) end, a second (also referred to interchangeably herein as a distal) end, and a marker exit positioned proximal to the second end, wherein the cannula is configure to receive a rod of a plunger for causing deploying a marker from the marker exit; a handle portion attached to or about the first end of the cannula; and a tapered adaptor portion attached to or about the cannula proximal to the first end of the cannula, the tapered adaptor portion being configured to engage an inner surface of a plurality of obturator sleeves into which the tapered adaptor portion is received.

Another aspect of the present disclosure provides a marker delivery device adaptor, comprising: a tapered adaptor portion configured to mate with a sleeve of a biopsy system, wherein the tapered adaptor portion is coaxial with and extends about or from the outer surface of a cannula, the cannula including: a proximal end, a distal end, and a marker exit positioned proximal to the distal end, wherein a rod is receivable within the cannula, the rod being capable of translating within the cannula deploying a marker from the marker exit; wherein the outer surface of the tapered adaptor portion tapers from a first end having a substantially oval cross section to a second end having a substantially circular cross section; and wherein the second end of the tapered adaptor portion is more proximal to the distal end of the cannula than the first end of the cannula.

Another aspect of the present disclosure provides a method of deploying a marker to a biopsy site, comprising: inserting a marker delivery device into an obturator sleeve the marker delivery device including: a cannula having a first end, a second end, and a marker exit positioned proximal to the second end; a rod being receivable within the cannula; and a tapered adaptor portion coupled to or about the first end of the cannula; engaging the tapered adaptor portion of the marker delivery device with the obturator sleeve via a friction fit; receiving the rod in the cannula; and traversing the received rod so to deploy the marker from the marker exit.

Figure 2:
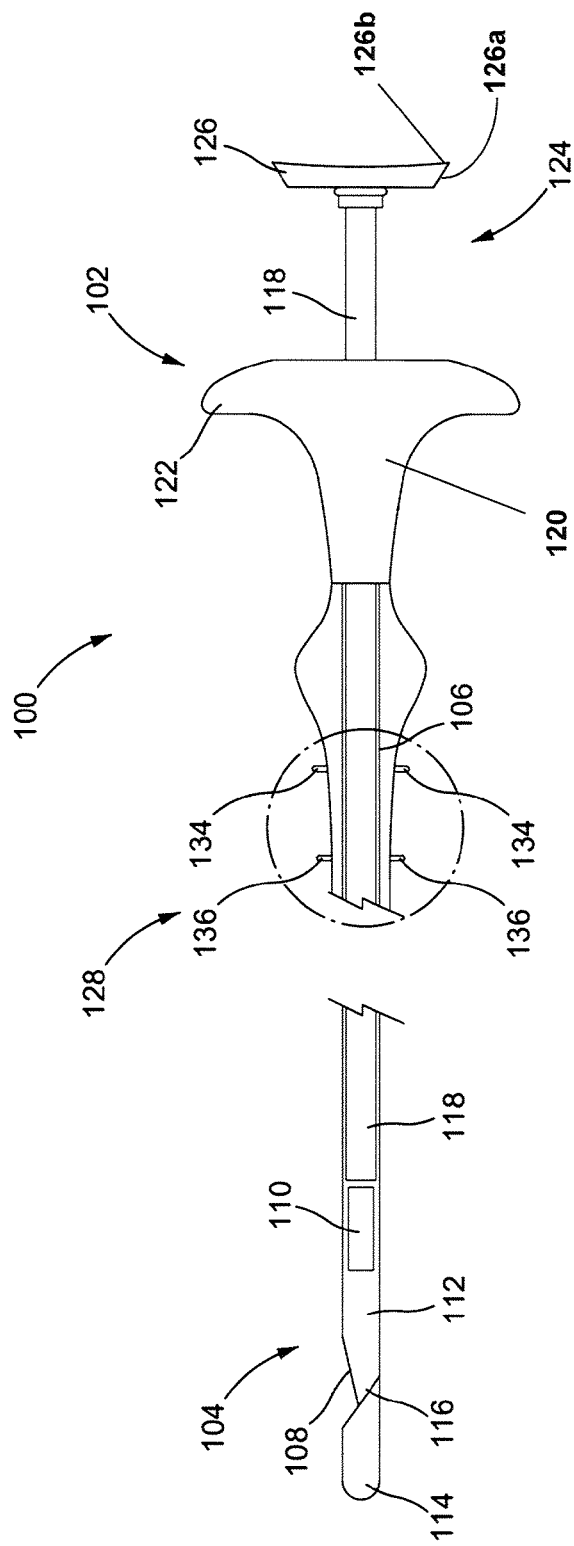
FIG. 2 is a side view of an example marker delivery device in accordance with aspects of the present disclosure.
Figure 3:
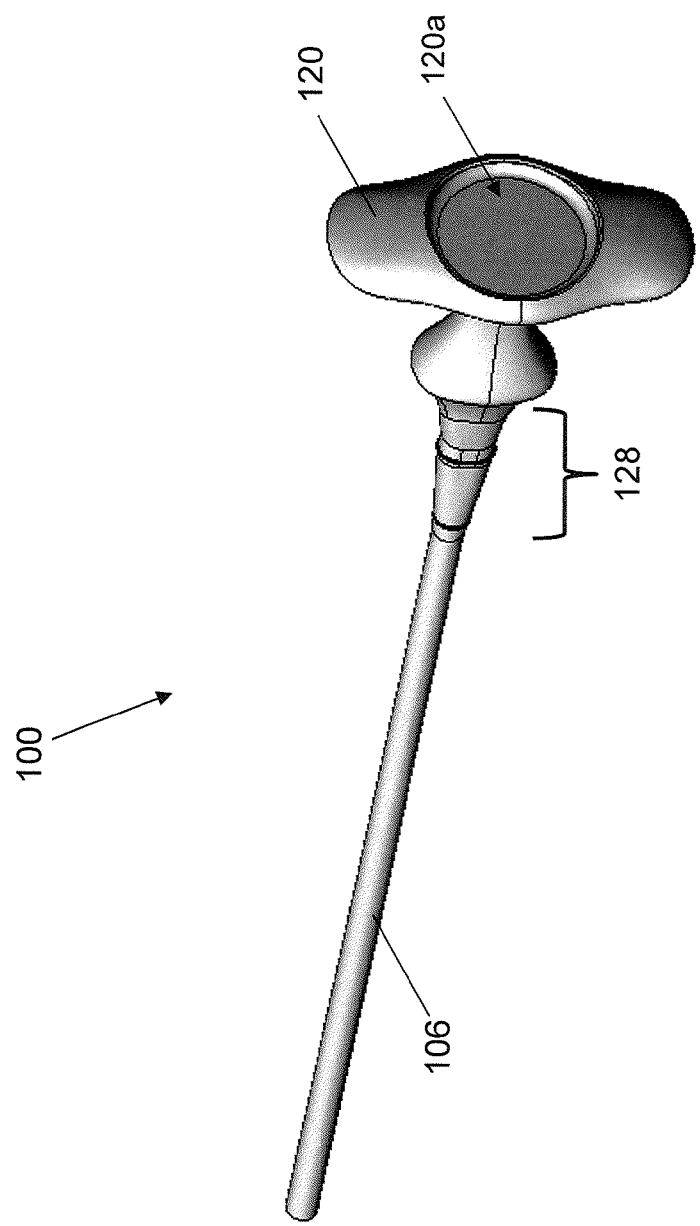
FIG. 3 shows a perspective view of the marker delivery device of FIG. 2.

FIG. 2 shows a side view of an example marker delivery device 100 in accordance with aspects of the present invention. FIG. 3 shows a perspective view of the marker delivery device 100 of FIG. 2. The marker delivery device 100 may include an operative end 102 (also interchangeably referred to herein as a first or proximal end) and a deployment end 104 (also interchangeably referred to herein as a second or distal end). The device 100 may include an elongated outer cannula portion 106 and a handle portion 120, the handle portion having one or more grip features 122. The cannula portion 106 may extend from the handle portion 120, or be attachably received within an opening in the handle portion 120, for example. The device 100 may also include a tapered adaptor portion 128, describe further below, that may, for example, be abuttably attached to the handle portion 120, and may also be attached to or extend about the cannula portion 106 at or near the first end 102 of the marker delivery device 100.

The deployment end 104 of the device 100 may include an opening 108 formed in the cannula 106. The opening 108 may be or comprise a side opening formed adjacent to, but spaced proximally from, the distal tip 114 of the cannula 106. A marker 110 may be disposed within a lumen 112 defined by the cannula 106 prior to deployment of the marker 110 from the device 100. The cannula 106 may terminate in a tip 114. A ramp 116 may be located at or near the tip 114. A plunger 124 receivable within the device 100 may include a rod portion 118 and a button 126. The device 100 may receive the rod portion 118 of a plunger 124 within the lumen 112 of the cannula 106. The rod portion 118, upon travel within the cannula 106, may act, for example, upon the received marker 110 during operation so as to deploy the marker 110 via the ramp 116 and opening 108.

The rod 118 of the plunger 124 may be caused to travel, for example, upon a user placing one or more fingers around the grip(s) 122 and depressing the button 126, such as with the user's thumb, for example. Travel of the rod 118 within the lumen 112 may thereby cause deployment of the marker 110 from the lumen 112 of the cannula 106 through the exit 108, for example, via the ramp 116. This operation may, for example, thereby be performed using a single hand of the user. Although rigid enough to cause travel of the marker 110 within the lumen 112, the rod 118 may also be generally flexible (such characteristic also being interchangeably referred to herein as "semi-rigid"). A spring or other biasing feature may be provided about rod 118 to bias the rod 118 in the direction A shown in FIG. 2, relative to the handle portion 120. For example, a spring may be positioned to encircle the rod 118 between the grip 122 and the plunger 126, such that the spring is biased from compression in direction A so as to oppose movement of the plunger 126 toward the handle portion 120.

Upon the received rod 118 having maximally traveled within the lumen 112, the button 126 may be receivable within a recess within the handle portion 120 (see, e.g., recess 120a shown in FIGS. 3, 7, 7A, and 7B). The recess may include one or more retaining features for retaining the button 126 within the recess. For example, as shown in the close up view of area A of FIG. 7, shown in FIGS. 7A and 7B, the recess 120a may include a lip or one or more protuberances 120b extending radially inwardly from the outer circumferential edge 120c of the recess 120. As shown in FIGS. 2 and 7B, for example, the button 126 may include a ramped or chamfered feature 126a, which may allow the edge of the button 126 to pass the lip or protuberences 120b, whereby upon the button 126 being fully received within the recess 120a, as further shown in the close up view of FIG. 7B, the button 126 may be retained within the recess via interaction of the lip or protuberances 120b with the edge 126b of the button 126. FIG. 7A shows a close up view of a portion of the handle 120 where the recess 120a and lip or protuberance 120b are located (absent the button 126 being shown as received in the recess 120a).

The cannula 106 may be formed of any suitable metallic or non-metallic material, and may be formed of a semi-rigid material. In some variations, the cannula 106 may be formed of a thin walled hollow tube, for example, comprising a suitable medical grade plastic or polymer. The cannula 106 may be formed of any suitable medical grade plastic or polymer, for example, as long as the medical grade plastic or polymer is suitable for the particular use, such as being substantially transparent to visible light and X-ray for some uses. The rod 118 may be formed of a similar or different material. The handle portion 120 may be formed from the same above-listed materials, as well.

The operative end 102 of the device 100 may include any suitable structure for allowing the operator to grip the device and actuate the rod 118. That is, the deployment features described herein are applicable to any suitable type of marker delivery device in which a rod is used to expel a marker. For example, the button, the handle portion, grip, and/or the plunger may be as disclosed in any of the above-noted references, e.g., U.S. Pat. Nos. 7,465,279; 6,996,433; 6,993,375; 7,047,063; 7,229,417; 7,044,957; 6,371,904; 8,371,443; 8,241,299; 8,068,895; 8,414,602, and/or U.S. Pub. Nos. 2013/0237912 and 2014/0276037, which are each incorporated by reference herein.

Figure 4:
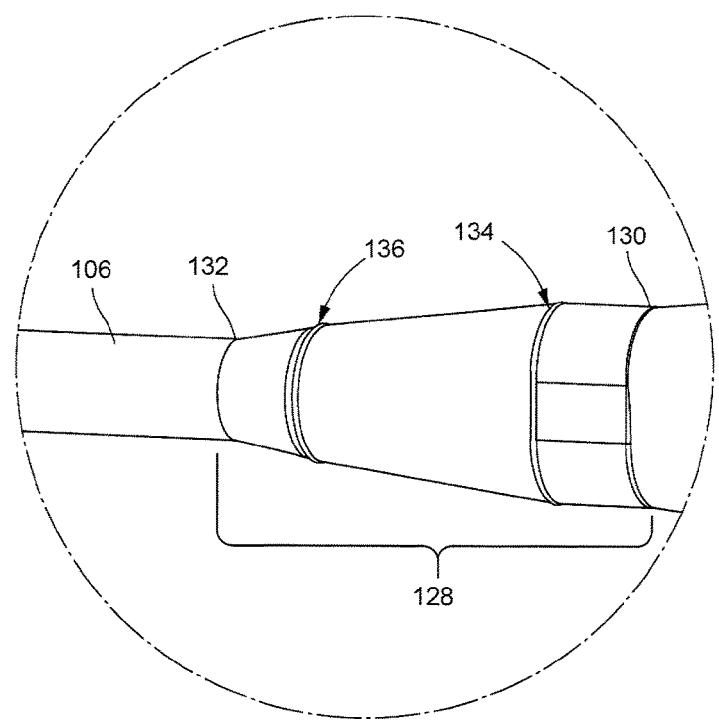
FIG. 4 is a close up partial perspective view of a portion of the marker delivery device of FIG. 2, in accordance with aspects of the present disclosure.
Figure 5:
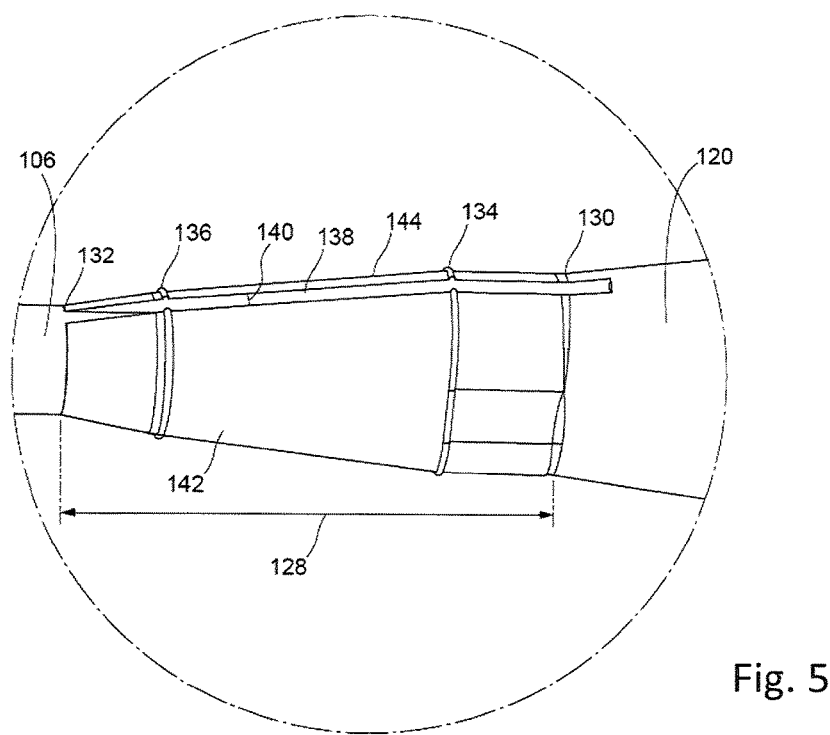
FIG. 5 is a close up partial perspective view of the marker delivery device of FIG. 2, rotated 90 degrees relative to FIG. 4, in accordance with aspects of the present disclosure.

FIGS. 4 and 5 show close up partial perspective and side views, respectively, of example variations and features of tapered adaptor portion 128, as shown in the dashed circle portion, of the marker delivery device 100 of FIG. 2, prior to mating of the marker delivery device 100 with a sleeve (see, e.g., sleeve 600 discussed further below with respect to FIGS. 7-9). FIG. 4 is a partial side perspective view of one example variation of the tapered adaptor portion 128 of the marker delivery device 100, and FIG. 5 is a view of the tapered adaptor portion 128 of FIG. 2 rotated about 90 degrees about the longitudinal axis of the marker delivery device 100 relative to the view shown in FIG. 4. As shown in FIGS. 4 and 5, the tapered adaptor portion 128 may abuttably extend from or extend about the cannula 106. In an aspect of the present disclosure, the tapered adaptor portion 128 may be integral with the hub 120, e.g., such that the hub 120 and the tapered adaptor portion 128 are formed as a single piece. In another aspect, the tapered adaptor portion 128 may comprise a separate piece that may be coupled with or attached to the cannula 106 and/or the tapered adaptor portion 128 at one end 132 of the tapered adaptor portion 128, as shown in FIGS. 4 and 5.

As shown in FIGS. 4 and 5, the tapered adaptor portion 128 may have a frustoconical shape, for example, where the inner diameter of the tapered adaptor portion 128 may be largest in perpendicular cross-sectional area at a point along its length axis at the first end 130, and the inner diameter of the tapered adaptor portion 128 may be smaller in perpendicular cross-sectional area at the second end 132 than at the first end 130, and may have a circular cross-sectional shape, for example, at its second end 132. The inner diameter of the tapered adaptor portion 128 may likewise gradually decrease along its length from the first end 130 to the second end 132. The tapered adaptor portion 128 may have an oval or elliptical cross-sectional shape at the first end 130, for example, with the cross-sectional shape varying from the oval or elliptical shape at the first end 130 to a circular or approximately circular cross-sectional shape at the second end 132. Other cross-sectional shapes may also be suitable, for example, oblong or other cross-sectional shapes. In an example aspect, the ratio of the inner diameter of at the first end 130 to the inner diameter at the second end 132 may be from between about 6:1 and 1.5:1, more preferably between about 5:1 and 2:1, and more further preferably between about 4:1 and 3:1.

As further shown in FIGS. 4 and 5, the tapered adaptor portion 128 may further comprise a first ridge or other protuberance or feature 134 and/or a second ridge or other protuberance or feature 136 extending radially outward from the outer surface of the tapered adaptor portion 128. The first ridge 134 may be located closer to the first end 130 than the second end 132, for example, while the second ridge 136 may be located closer to the second end 132 than the first end 130. The first ridge 134 and the second ridge 132 may be positioned along the tapered adaptor portion 128 at predetermined positions, for example, to assist in engagement and/or provide indication that the tapered adaptor portion 128 is engageably in contact with each of at least two differently shaped sleeves at different receiving points within the sleeves, as discussed in more detail below. For example, one of the ridges may engageably contact at least a portion of a first sleeve to assist with positioning of the marker delivery device 100 relative to the first sleeve, while the second ridge may engageably contact at least a portion of a second sleeve to assist with positioning the marker delivery device relative to the second sleeve.

The tapered adaptor portion 128 of FIG. 2 may further include a slot 138 (FIG. 5) extending along the length of the tapered adaptor portion 128. The slot 138 may extend from the first end 130 to the second end 132, as shown in FIG. 5. A second slot (not shown in FIG. 5) may be provided on the radially opposite side of the tapered adaptor portion 128, for example, dividing the tapered adaptor portion 128 into two opposing segments 142, 144 (such segments also interchangeably referred to herein as subportions of the tapered adaptor portion). The width 140 and/or length, for example, of the slots may be selected so as to allow the user to readily and easily collapse, such as by pinching, the opposing segments toward each other, as described in more detail below. The ratio of the width of the slot 138 to the inner diameter of the cannula 106 may be between about 1:15 and 1:3, and more preferably between about 1:13 and 1:5, and more further preferably between about 1:10 and 1:6.

Figure 6A:
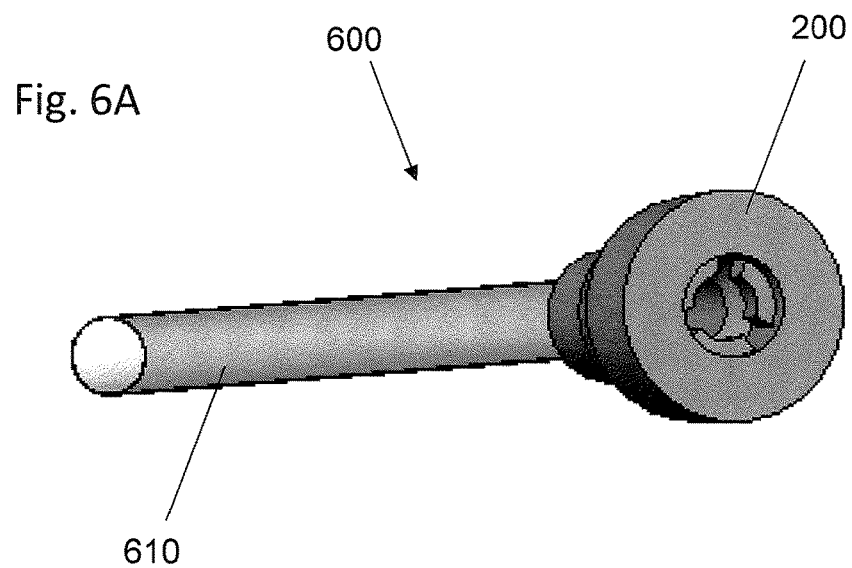
FIG. 6A shows a perspective view of a first example obturator sleeve for use in accordance with aspects of the present disclosure.

FIG. 6A shows a perspective view of a first example obturator sleeve 600 for use in accordance with aspects of the present disclosure. The first sleeve 600 includes a hub portion 200 and a cannula portion 610, the cannula portion 610 being abuttably attached to the hub portion 200, for example, or the cannula portion 610 being fixedly received within the hub portion 200.

Figure 6B:
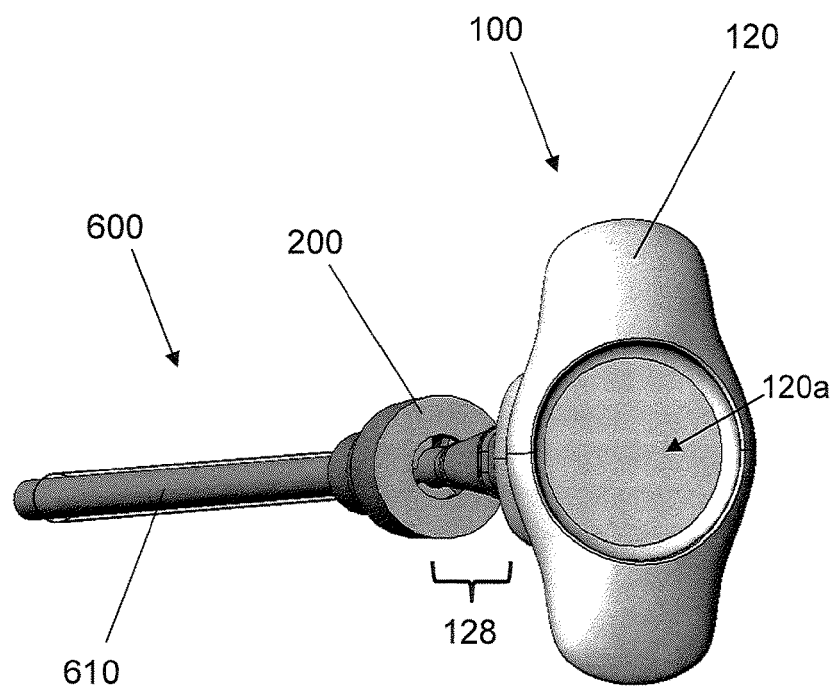
FIG. 6B shows a perspective view of an example marker delivery device received within the obturator sleeve of FIG. 6A.

FIG. 6B shows a perspective view of the example marker delivery device 100 received within the obturator sleeve 600 of FIG. 6A.

FIG. 7 shows a cross sectional view of the marker delivery device 100 and sleeve 200 of FIG. 6B. FIG. 7 shows the marker delivery device 100, upon being partially inserted into a hub 200 of first sleeve 600 (FIG. 6B) to an insertion point prior to the tapered adaptor portion 128 being received within the hub 200. The hub 200 may be used in combination with a biopsy device for taking a biopsy sample, for example, similar to as shown and described with regard to FIG. 1. As noted above, prior to marking a biopsy site, the biopsy process may include first puncturing tissue with a puncture needle receivable within the sleeve 600 (FIG. 6B). It is noted that the puncturing needle may also include the sleeve 600 (FIG. 6B). Next, if the puncture needle is separate from the sleeve 600 (FIG. 6B), the puncture needle may be removed from the sleeve 600 (FIG. 6B). The sleeve 600 (FIG. 6B) remains retained in a fixed position (e.g., via the grid 34 of FIG. 1 and/or relative to tissue in which the sleeve 600 of FIG. 6B extends). Then, a biopsy device may be inserted into the sleeve 600 (FIG. 6B) to remove a tissue sample from the biopsy site. The biopsy device may then be removed, and a marker delivery device (e.g., marker delivery device 100 of FIG. 2) may be inserted into the sleeve 600 (FIG. 6B). The sleeve 600 (FIG. 6B) may have a particular geometry for cooperative use with the particular biopsy device involved. For example, referring to FIGS. 8, 9, 14, and 15, the hub 200 of sleeve 600 (FIG. 6B) may include an entrance portion 202 having a three piece hard stop 204 adjacent the entrance portion 202. Opposite the three piece hard stop 204 from the entrance portion 202, the hub 200 may include a taper portion 206 (also interchangeably referred to herein as a "distal taper") gradually reducing the inner diameter of the hub 200.

Figure 8:
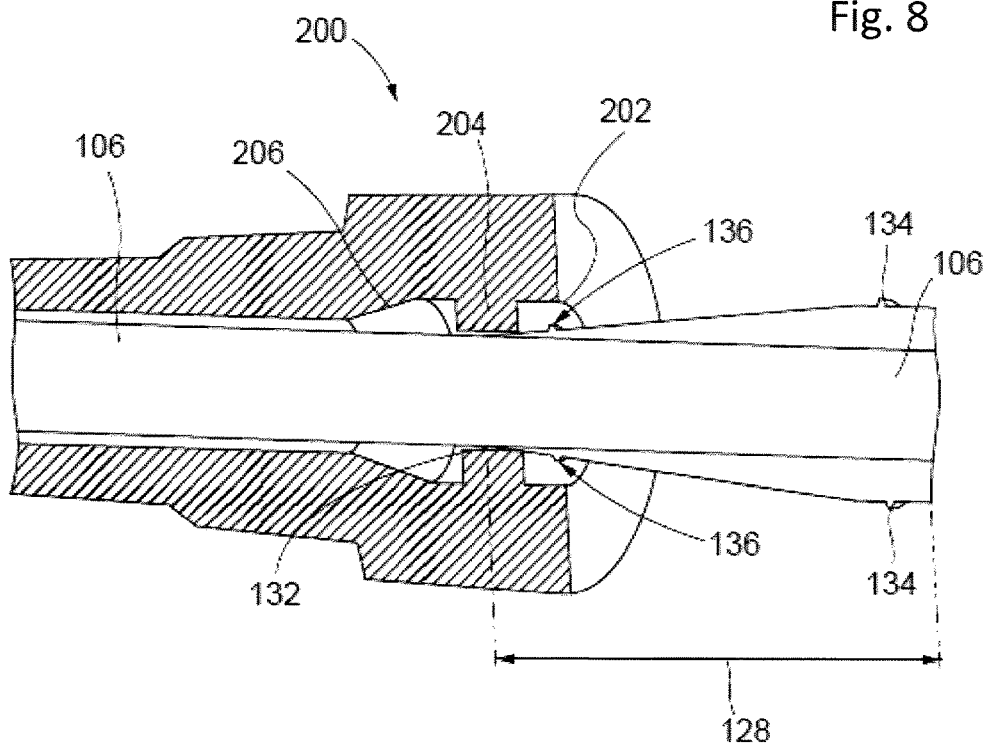
FIG. 8 is a partial close up cross-sectional view of the example marker delivery device of FIG. 2 partially inserted into the first sleeve, with omissions, in accordance with aspects of the present disclosure.
Figure 9:
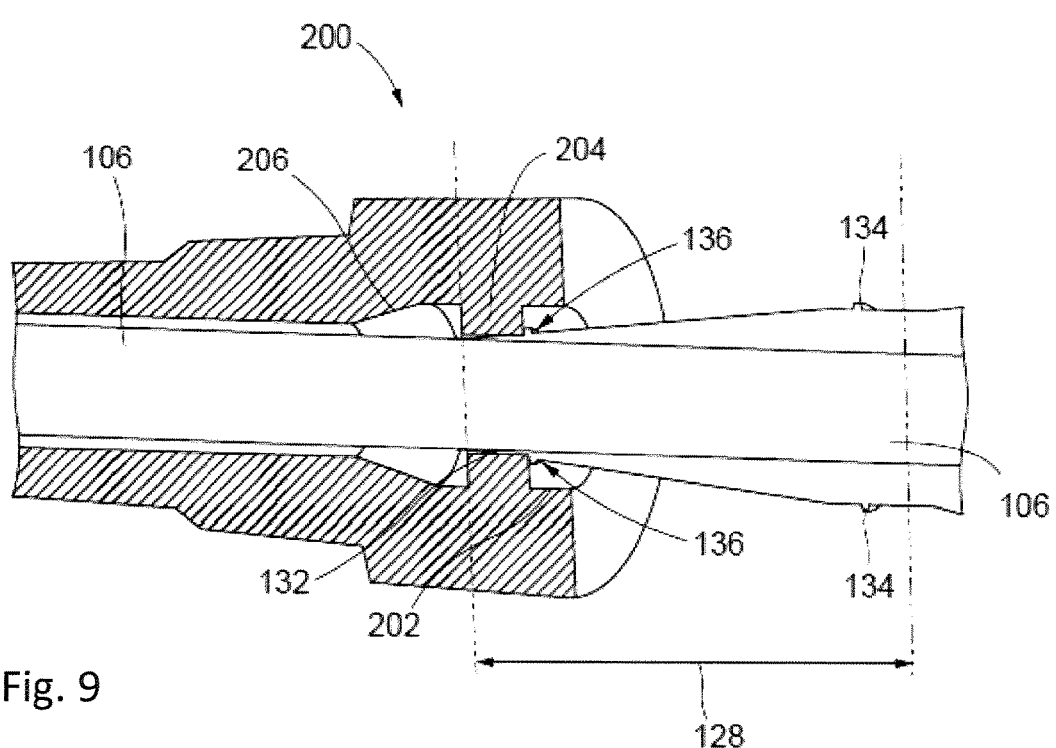
FIG. 9 is a partial close up cross sectional view of the example marker delivery device of FIG. 2 fully inserted into the first sleeve, with omissions, in accordance with aspects of the present disclosure.
Figure 14:
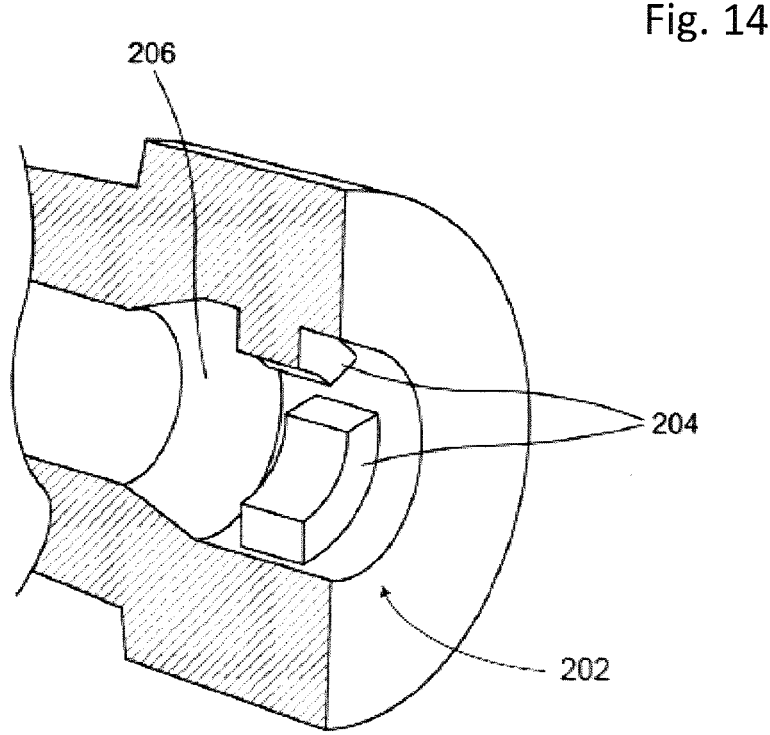
FIG. 14 shows a cut-away view of an entrance portion and a three piece hard stop of the example marker delivery device of FIG. 2, in accordance with aspects of the present disclosure.
Figure 15:
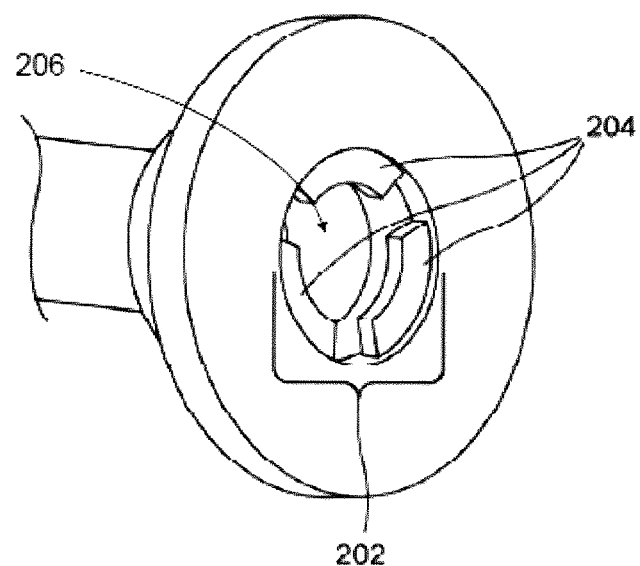
FIG. 15 shows a distal taper and three individual pieces of the three piece hard stop of the example marker delivery device of FIG. 2, in accordance with aspects of the present disclosure.

FIG. 8 shows a close up cross-sectional view of a portion of the marker delivery device 100 of FIG. 2 being received within the hub 200 to a position just before the second ridge 136 would contact the three piece hard stop 204, if the device 100 were to be further inserted into the hub 200. FIG. 14 shows a cut-away view of the entrance portion 202 and three piece hard stop 204. FIG. 15 shows the distal taper 206 and all three individual pieces of three piece hard stop 204.

At this point in the procedure, because of its taper aspects, for example, the tapered adaptor portion 128 of the marker delivery device 100 may frictionally fit within the space defined by the three piece hard stop 204. The user may continue to push the marker delivery device 100 through the hub 200, thereby wedging the tapered adaptor portion 128 of the marker deliver device 100 into the partial circular opening formed by the three piece hard stop 204. Because the outer diameter of the taper section 128 of the marker delivery device 100 may increase toward the first end 130, the further the operator pushes the marker delivery device 100 into the hub 200, the tighter the frictional fit may become. Eventually, it may become difficult to push the marker delivery device 100 any further into the hub 200. Tactile feel of contact of the ridge 136 with a hard stop 204 may also assist the user in determining that the marker delivery device 100 has been properly fully received in the sleeve 600 (FIG. 6B).

The size and rate of increase (e.g., the slope) of the outer diameter of the tapered adaptor portion 128 of the marker delivery device 100, as well as the position of the second ridge 136 along the tapered adaptor portion 128, may be selected such that when sufficient friction fit occurs between the taper portion 128 and the sleeve 200, and/or the second ridge 136 contacts the three piece hard stop 204, the opening of 108 of the marker delivery device 100 may thereupon be placed in a proper location within the biopsy site (e.g., such that the opening 108 is placed in a proper location for delivery of the marker 110 with relation to the sleeve). Thus, for example, if the sleeve 600 includes an exit portion, the opening 108 of the marker delivery device may align with the exit portion when the second ridge 136 contacts the three piece hard stop 204. With this configuration and operation, once the user has fully inserted the marker delivery device 100 into the hub 200 of the sleeve 600 (FIG. 6B), the user may thereby ascertain that the opening 108 is properly located (e.g., for marker deployment at or near the biopsy location).

In another aspect of the present disclosure, the hub 200 may include an annular recess (not shown) having approximately the same or slightly larger dimensions as the second ridge 136. For example, the recess may be located at the surface of the three piece hard stop 204 at the point of contact with the second ridge 136 as shown in FIG. 9. When the recess is included, the user may further experience a tactile sensation of the second ridge 136 entering into the recess, for example. Furthermore, the user may hear an audible sound, such as a click when the second ridge 136 enters such recess. The tactile and/or audible feedback may thereby further allow the operator to determine that the deployment marker delivery device 100 is in the fully inserted position and that no further force in deployment is necessary.

To release the marker delivery device 100 from the sleeve 200, the operator may collapsably compress (e.g., by pinching) the opposing segments 142, 144 (FIG. 5), such as by pressing the opposing segments toward one other. The compressing force may thereby partially collapse the slot 138, thereby enabling disengagement of the marker delivery device 100 from the hub 200. The user may then freely pull the marker delivery device 100 out of the sleeve 600 (FIG. 6B).

Figure 10A:
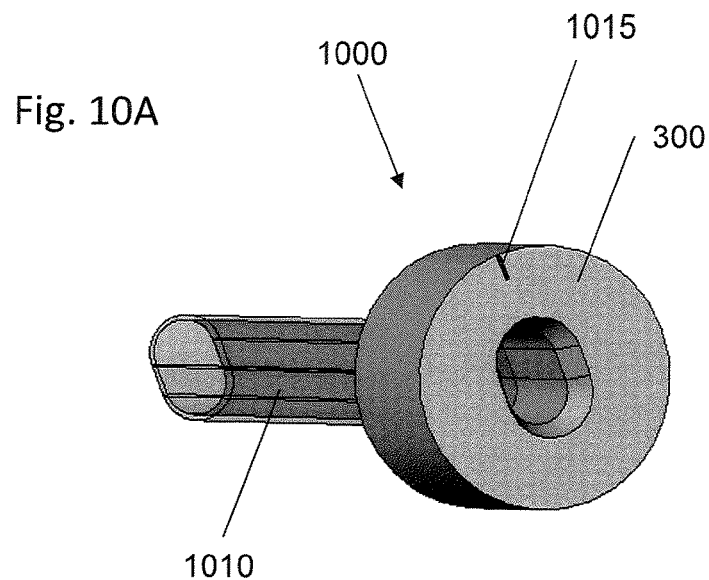
FIG. 10A shows a perspective view of a second example obturator sleeve for use in accordance with aspects of the present disclosure.

FIG. 10A shows a perspective view of a second example obturator sleeve 600 for use in accordance with aspects of the present disclosure. The sleeve 1000 includes a hub portion 300 and a cannula portion 1010, the cannula portion 1010 being abuttably attached to the hub portion 300, for example, or the cannula portion 1010 being fixedly received within the hub portion 300. As shown in FIG. 10A, the hub portion 300 may optionally include an indicator 1015, such as a mark or groove on the hub portion 300 that may be used for alignment purposes between the obturator sleeve 1000 and a received marker delivery device, as described further below in conjunction with FIG. 10B.

Figure 10B:
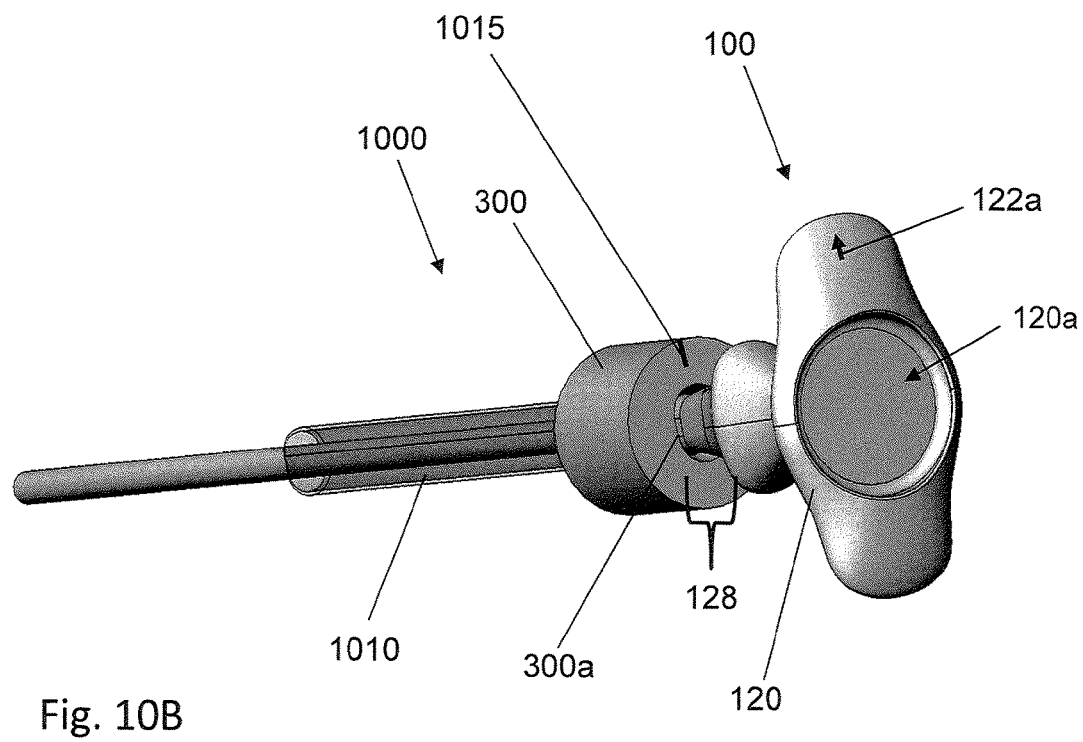
FIG. 10B shows a perspective view of the example marker delivery device received within the obturator sleeve of FIG. 10A.

FIG. 10B shows a perspective view of the example marker delivery device 100 received within the obturator sleeve 1000 of FIG. 10A. As shown in FIG. 10B, the marker delivery device 100 may optionally have (e.g., on its surface) a mark or other indicator 122a and/or wording to assist with alignment of the marker delivery device with the obturator sleeve 1000. For example, such alignment may be needed with some obturator devices to ensure that the opening for deploying the marker (see, e.g., opening 108 in marker delivery device 100 shown in FIG. 1) aligns properly with a corresponding opening or other feature in the obturator sleeve 1000 so as to enable marker deployment.

In use, for example, as shown in FIG. 10B, the tapered adaptor portion 128 may have an elliptically cross-sectionally shaped outer surface that is receivable within a corresponding elliptically cross-sectionally shaped opening 300a in the hub portion 300 of the obturator sleeve 1000. As shown in FIG. 10B, the indicator 122a on the handle portion 120 of the marker delivery device 100 may be aligned by the user with the indicator 1015 on the hub portion 300 of the obturator sleeve 1000 in order to ensure that the marker delivery device 100 is not oriented 180 degree opposite the correct direction for alignment of the opening in the obturator sleeve 1000 with the corresponding opening (e.g., opening 108 of FIG. 1) of the marker delivery device 100 for deployment of the marker via the opening.

Figure 11:
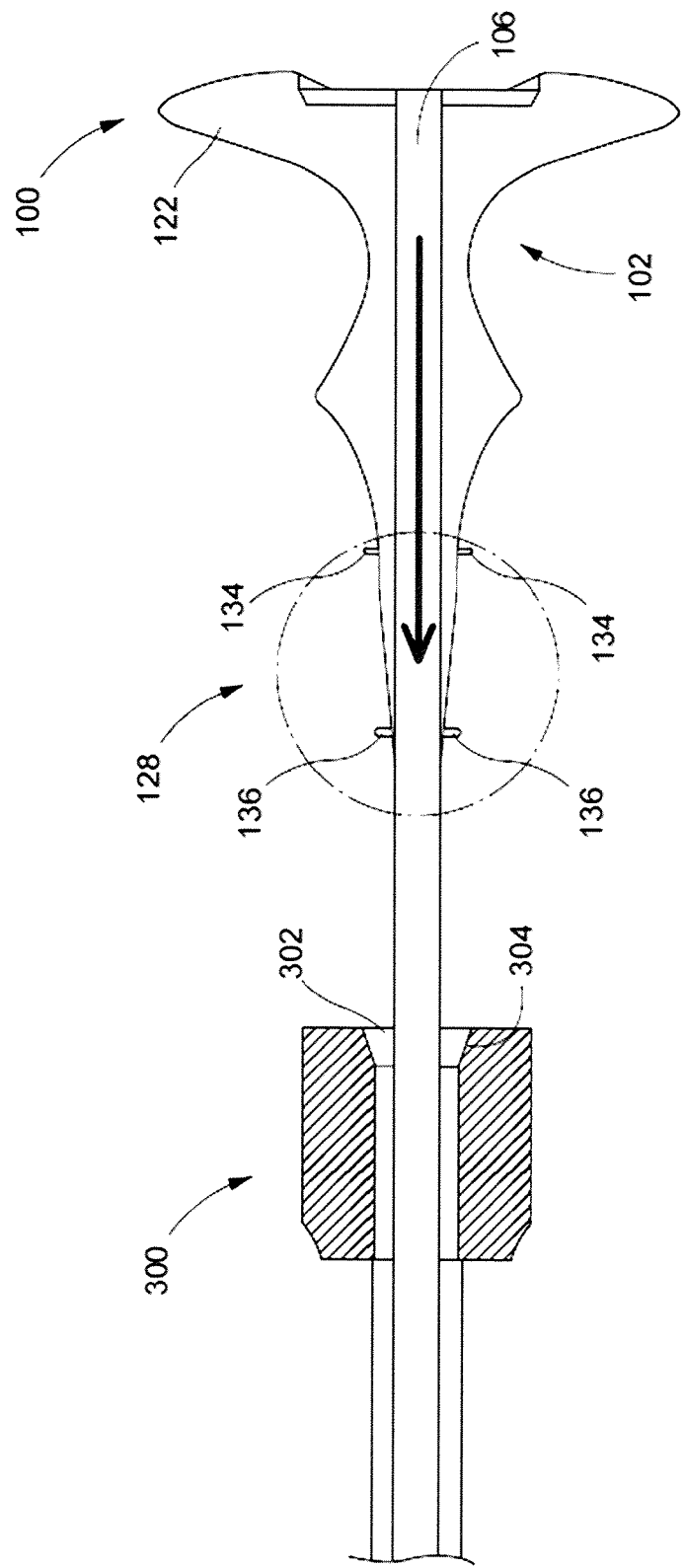
FIG. 11 is a cross-sectional view of the example marker delivery device of FIG. 2 partially inserted into a second sleeve, with omissions, in accordance with aspects of the present disclosure.

FIG. 11 shows a cross sectional view of the marker delivery device 100 upon partial initial insertion into the hub 300 of sleeve 1000 (FIG. 10B), prior to the tapered adaptor portion 128 being inserted to a point so as to be received within the hub 300. The sleeve 300 may be used in combination with a biopsy device, and in particular, a biopsy device differing in dimensions and/or features from the device using hub 200 and sleeve 600 of FIGS. 6A-9, 14, and 15. As noted above, prior to marking a biopsy site, the biopsy process may include first puncturing the tissue with a puncture needle within the sleeve 1000 (FIG. 10B). Next, the puncture needle may be removed from the sleeve 1000 (FIG. 10B), with the sleeve 1000 being held in a fixed position (e.g., via the grid 34 of FIG. 1 and/or relative to tissue in which the sleeve 1000 of FIG. 10B extends). Then, a biopsy device may be inserted into the sleeve 1000 (FIG. 10B) to remove a tissue sample from the biopsy site. The biopsy device may then be removed, and the marker delivery device 100 may be inserted into the sleeve 1000 (FIG. 10B). The sleeve 1000 (FIG. 10B) may be a second type of sleeve having a particular geometry for use, for example, in a particular biopsy system. For example, also referring to FIGS. 12 and 13, the hub 300 of sleeve 1000 (FIG. 10B) may include an entrance portion 302 leading into a proximal taper 304 that gradually reduces the inner diameter of the hub 300.

FIG. 12 shows a close up cross-sectional view of marker delivery device 100 being inserted into the hub 300 of sleeve 1000 (FIG. 10B) to a position just before the first ridge 134 contacts the end of the proximal taper 304. At this point in the procedure, because of the taper of the tapered adaptor portion 128, the tapered adaptor portion 128 may be able to frictionally fit within the space defined by the end of the proximal taper 304 of the hub 300. The operator may continue to push the marker delivery device 100 through the hub 300, thereby wedging the tapered portion 128 into the space defined by the end of the proximal taper 304. Because the outer diameter of the taper section 128 may increase toward the first end 130 (FIG. 7), the further the operator pushes the marker delivery device 100 into the hub 300, the tighter the frictional fit may become. Eventually, it may become difficult to push the marker delivery device 100 any further into the hub 300 of sleeve 1000 (FIG. 10B).

Notably, because the portion of the hub 300 defined by the end of the proximal taper 304 in FIG. 10B may be larger in internal diameter than the space defined by the three piece hard stop 204 of the hub 200 (FIG. 6B), the marker delivery device 100 may be pushed much farther into the hub 300 of FIG. 10B as compared to the hub 200 (FIG. 6B). As seen in FIGS. 12 and 13, the taper portion 128 may not contact the hub 300 until the hub 300 reaches a point on the taper portion 128 near the end 130. For the same reason, the second ridge 136 may not contact the hub 300 at any point during the insertion. Thus, the second ridge 136 may be received much farther within the hub 300 than the second ridge 136 is received within the sleeve 200 (FIG. 6B) during insertion. However, because the outer diameter of the taper portion 128 may be larger near the end 130, eventually, during insertion, the taper portion 128 may contact the hub 300. Upon continued insertion, the same friction fit described above may occur within the second hub 300, but may occur near the end 130, instead of closer to the end 132. Thus, the taper portion 128 allows the same marker delivery device 100 to be used in combination with a biopsy system using the sleeve 200 (FIG. 6B) or the sleeve 300 (FIG. 10B).

The sizes and rate of increase (e.g., the slope of taper) of the outer diameter of the taper portion 128, as well as the position of the first ridge 134 along the tapered adaptor portion 128 may be selected such that when the friction fit occurs and the first ridge 134 contacts the end point of the proximal taper 304, the opening of 108 of the marker delivery device 100 may be in a selected location relative to the biopsy site (e.g., such that the marker exit is located at or near the biopsy site location). With this configuration, once the user has fully inserted the marker delivery device 100 into the hub 300, the user may ascertain that the opening 108 is properly located at the biopsy location. Further, the sleeve may include an exit portion (not shown), and the opening 108 of the marker delivery device may align with the exit portion when the first ridge 134 contacts the end point of the proximal taper 304.

In another aspect of the present disclosure, the hub 300 may include an annular recess (not shown) having approximately the same or slightly larger dimensions than the first ridge 134. For example, the recess may be located within the inner surface of the hub 300 at the point of contact of the first ridge 134 with the hub 300, as shown in FIG. 13. When the recess is included, the user may experience a tactile sensation of the first ridge 134 entering into the recess. Furthermore, the user may hear an audible sound, such as a click when the first ridge 134 enters the recess. The tactile and/or audible feedback may further let the operator know that the deployment marker delivery device 100 is in the fully inserted position and no further force is necessary. To release the marker delivery device 100 from the sleeve 1000 (FIG. 10B), the operator may press with a squeezing force on the opposing segments 142, 144 (FIG. 5), such as by pressing the opposing segments toward each other. The squeezing force may compress the slot 138, thereby freeing the engagement with the hub 300. The user may then freely pull the marker delivery device 100 out of the sleeve 1000 (FIG. 10B).

The marker delivery device described herein may be used in conjunction with any suitable biopsy device known in the art used as part of a biopsy procedure. For example, the marker delivery device may be used in conjunction with any of the biopsy devices described in U.S. Pat. Nos. 5,526,822; 6,086,544; 6,626,849; 7,442,171; 7,938,786; 8,118,755; 9,095,326; 8,251,916; and/or 8,532,747, which are incorporated by reference.

An example method of operating the marker delivery device 100 will now be described. As noted above, the operator may first take a biopsy from a biopsy site using a biopsy device. Taking the biopsy may include first puncturing the tissue with a puncture needle within one of the sleeves 600, 1000. Next, the puncture needle may be removed from the sleeve 600, 1000, with the sleeve 600, 1000 being held in the same position. Then, a biopsy device may be inserted into the sleeve 600, 1000 to remove one or more tissue samples from the biopsy site. The biopsy device may then be removed, and the marker delivery device 100 may be inserted into the sleeve 600, 1000. The user may continue to extend the marker deployment device 100 into the sleeve until the frictional fit of the taper portion 128 engaged with the hub 200, 300 of sleeve 600, 1000, respectively, prevents further movement and/or until the first or second ridge 134, 136 engages contacts or otherwise engages the hub 200, 300. In the case of the sleeve 600, the friction fit may occur near the second end 132, and the second ridge 136 may contact the hub 200. In the case of the sleeve 1000, the friction fit may occur near the first end 130, and the first ridge 134 may contact the hub 300. In either case, the open end 108 may thereby be located within or near the biopsy site due to the relative shape, size, and positioning of the taper portion 128 and/or the first and second ridges 132, 134 relative to the sleeve 600 or 1000.

Next, the operator may actuate the marker delivery device 100 to release the marker 110 from the cannula 106. For example, the operator may begin to apply force on the plunger 126 to translate the rod 118 toward the tip 114 at the distal end of the cannula 106. As noted above, the movement of the rod 118 may be achieved by any known actuation mechanism, and in particular, the mechanism disclosed in the U.S. Patents and U.S. Patent Application Publications incorporated by reference above. As the rod 118 translates, the rod may push the marker 110 up the ramp 116 and out the opening 108. The marker 110 may thus be delivered to the biopsy site.

After the marker 118 has been delivered, the operator may apply a squeezing force of the opposing segments 142, 144, which may release the friction fit of the taper portion 128 with the hub 200, 300. Once disengaged, the operator may remove the marker delivery device 100 from the sleeve 600, 1000.

The marker may be any suitable marker known in the art. For example, as described in U.S. Pat. No. 8,068,895 (which is hereby incorporated by reference), the marker may comprise a marker body and a marking element. In some variations, the marker body may be visible under ultrasound imaging, while the marking element may be visible under MRI and/or X-ray, among other imaging modalities. For instance, the marker body may be formed of bovine collagen, cellulose, polylactic acid/polyglycolide, glycoprene, gelatinous materials such as hydrogel, and/or any other suitable material(s), including combinations thereof. Furthermore, the marker body may be biodegradable or bioabsorbable, or may have other properties. The marking element may comprise a titanium wire, pellet, or other structure. Any other suitable material(s) and/or combination(s) of material(s) may be used for the marking element, provided the marking element may be visible under MRI and/or X-ray, among other imaging modalities. In some variations, the marker body may be formed of a square collagen pad that is folded and/or rolled about a titanium marking element to form a substantially cylindraceous marker. The marker may then be compressed radially inward in this example before being inserted into the cannula for deployment. The marker may have a variety of alternative configurations, may be formed using a variety of techniques, and may be used in a variety of other ways as described in some of the U.S. Patents and U.S. Patent Application Publications incorporated by reference above.

Aspects of the present disclosure provide a means for deploying implantable biopsy site markers with repeatable alignment, physical user feedback and compatibility with MRI, and stereotactic coaxial biopsy introducer sleeves. Aspects of the present disclosure are believed to work well with all commercially available biopsy devices. One example embodiment in accordance with aspects of the present disclosure works with commercially available devices such as Mammotome Legacy MR, Mammotome Revolve MR, both available from Devicor Medical Products Inc. Aspects of the present disclosure are also believed to work well with Hologic Suros Eviva ST, available from Hologic Inc. Aspects of the present disclosure are believed to offer improved ease of removal from commercially available biopsy devices due, for example, to the "pinch release" feature.

While various example features have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects of the present disclosure, as set forth above, are intended to be illustrative, not limiting. Various changes may be made without departing from the spirit and scope hereof. Therefore, aspects of the disclosure are intended to embrace all known or later-developed alternatives, modifications, variations, improvements, and/or substantial equivalents.

KEY TO FIGURES

Number Part Names
100 Deployment marker delivery device
102 Operative end
104 Deployment end
106 Cannula
108 Opening
110 Marker
112 Lumen
114 Tip
116 Ramp
118 Rod
120 Handle portion
120a Recess
120b Protuberance
120c Recess outer circumferential edge
122 Grip
122a Alignment indicator on handle portion
124 Plunger
126 Button
126a Tapered edge of button
126b Edge of button
128 Tapered adaptor portion
130 First end
132 Second end
134 First ridge
136 Second ridge
138 Slot
140 Width
142 Opposing segments
144 Two opposing segments
200 Hub of first sleeve
202 Entrance portion
204 Piece hard stop
206 Distal taper
300 Hub of second sleeve
300a Opening in hub portion
302 Entrance portion
304 Proximal taper
600 First sleeve
610 First sleeve cannula portion
1000 Second sleeve
1010 Second sleeve cannula portion
1015 Alignment indicator on second sleeve

The invention claimed is:

1. A marker delivery device for marking a biopsy site, comprising:
 a cannula having a proximal end, a distal end, and a marker exit proximate to the distal end, wherein the cannula is configured to receive a marker deploying rod for deploying a marker through the marker exit;
 a handle; and
 a tapered adaptor portion disposed between the handle and the proximal end of the cannula, the tapered adaptor portion being configured to engage different inner surfaces of a plurality of obturator sleeves into which the tapered adaptor portion is received, wherein the tapered adaptor portion includes:
  an outer surface,
  a first radially extending feature extending from the outer surface of the tapered adaptor portion, and
  a second radially extending feature extending from the outer surface of the tapered adaptor portion,
 wherein the tapered adaptor portion engages each of the different inner surfaces of the plurality of obturator sleeves at a position defined by one of the first radially extending feature or the second radially extending feature.

2. The marker delivery device of claim 1, wherein the position defined by one of the first radially extending feature or the second radially extending feature is a position of the marker exit.

3. The marker delivery device of claim 1, wherein the first radially extending feature and second radially extending feature comprise a semi-rigid material.

4. The marker delivery device of claim 1, wherein the marker deploying rod has a first end and a second end, the marker deploying rod further comprising:
 a plunger button connected to the first end of the marker deploying rod.

5. The marker delivery device of claim 4, wherein the handle further comprises:
 a grip;
 wherein the grip and the plunger button are cooperatively actuable so as to cause the marker deploying rod to traverse within the cannula.

6. The marker delivery device of claim 5, wherein the grip and the plunger button are cooperatively actuable by one hand of a user.

7. The marker delivery device of claim 4, wherein the tapered adaptor portion has a first and a second end, wherein the handle has a first end and a second end, wherein the first end of the tapered adaptor portion is proximal the second end of the handle, and wherein first end of the handle has a recess.

8. The marker delivery device of claim 7, wherein the plunger button is receivable within the recess of the handle.

9. The marker delivery device of claim 7, further comprising:
 a biasing device positioned between the plunger button and the handle.

10. The marker delivery device of claim 8, wherein the recess comprises:
 an inner surface; and
 a protuberance extending from the inner surface;
 wherein the plunger button, upon being receive within the recess of the handle, is retained therein by the protuberance.

11. The marker delivery device of claim 10, wherein the protuberance includes a lip.

12. The marker delivery device of claim 1, wherein the tapered adaptor portion further comprises:

an inner surface facing a direction opposite the outer surface of the cannula; and
a slot, dividing the tapered adaptor portion into at least two subportions.

13. The marker delivery device of claim 12, wherein the tapered adaptor portion is disengageable from each of the different surfaces of the plurality of obturator sleeves via application of a collapsably compressing force on the at least two subportions of the tapered adaptor portion.

14. The marker delivery device of claim 1, wherein each of the plurality of obturator sleeves includes a hub, and wherein each of the different inner surfaces of each of the plurality of obturator sleeves into which the tapered adaptor portion is receivable comprises an inner surface of the hub.

15. The marker delivery device of claim 7, wherein the tapered adaptor portion has an axial length, wherein the tapered adaptor portion has an outer surface, and wherein the outer surface defines a cross-sectional area along the axial length of the tapered adaptor portion; and
wherein the cross-sectional area defined by the outer surface of the tapered adaptor portion at the second end is less than the cross-sectional area of the outer surface of the tapered adaptor portion at the first end.

16. The marker delivery device of claim 15, wherein the outer surface of the tapered adaptor portion encompassing the cross-sectional area at the second end defined by a circle.

17. The marker delivery device of claim 15, wherein the outer surface of the tapered adaptor portion encompassing the cross-sectional area at the first end is defined by an oval or an ellipse.

18. The marker delivery device of claim 1, wherein the handle has an alignment indicator, and wherein the marker deliver device further includes:
a marker delivery device alignment indicator;
wherein the handle is alignable relative to the marker delivery device via the handle alignment indicator and the marker delivery device alignment indicator.

19. A marker delivery device, comprising:
a cannula having a proximal end, a distal end, and a marker exit positioned proximal to the distal end; and
a tapered adaptor portion extending about or from the outer surface of the cannula, wherein the tapered adaptor portion has a first end, a second end, a body, and an opening extending in an axial direction from the body from the first end to the second end, wherein the outer surface of the tapered adaptor portion tapers from a first end having a substantially oval cross section to a second end having a substantially circular cross section, wherein the second end is more proximal to the distal end of the cannula than the first end.

20. The marker delivery device of claim 19, further comprising:
a first ridge extending from the body adjacent the first end; and
a second ridge extending from body adjacent the second end, wherein the first ridge and the second ridge each extend to differing outer diameters from the outer surface of the tapered adaptor portion.

21. The marker delivery device of claim 20, wherein the outer diameter of the first ridge is greater than the outer diameter of the second ridge.

22. The marker delivery device of claim 20, wherein at least a portion of the first end of the tapered adaptor portion is configured to engage an inner radial surface of a first obturator sleeve, and at least a portion of the second end of the tapered adaptor portion is configured to engage an inner radial surface of a second obturator sleeve, and wherein the radial inner surface of the first obturator sleeve has a different cross-sectional shape than the cross-sectional shape of the radial inner surface of the second obturator sleeve.

23. A marker delivery device adaptor, comprising:
a tapered adaptor portion configured to mate with a sleeve of a biopsy system, wherein the tapered adaptor portion is coaxial with and extends about or from the outer surface of a cannula, the cannula including:
a proximal end,
a distal end, and
a marker exit positioned proximal to the distal end, wherein a rod is receivable within the cannula, the rod being capable of translating within the cannula deploying a marker from the marker exit;
wherein the outer surface of the tapered adaptor portion tapers from a first end having a substantially oval cross section to a second end having a substantially circular cross section; and
wherein the second end of the tapered adaptor portion is more proximal to the distal end of the cannula than the first end of the cannula.

24. The marker delivery device adaptor of claim 23, wherein the cannula is formed of a material that is substantially transparent to visible light and X-ray.

25. A method of deploying a marker to a biopsy site, the method comprising:
inserting a marker delivery device into an obturator sleeve, the marker delivery device including:
a cannula having a first end, a second end, and a marker exit positioned proximal to the second end;
a rod being receivable within the cannula; and
a tapered adaptor portion coupled to or about the first end of the cannula;
engaging a protuberance extending from the tapered adaptor portion of the marker delivery device with the obturator sleeve via a friction fit;
receiving the rod in the cannula; and
traversing the received rod so to deploy the marker from the marker exit.

* * * * *